US012498357B2

(12) United States Patent
Iwata

(10) Patent No.: US 12,498,357 B2
(45) Date of Patent: Dec. 16, 2025

(54) AMINO ACID ANALYSIS METHOD

(71) Applicant: SHIMADZU CORPORATION, Kyoto (JP)

(72) Inventor: Natsuki Iwata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 728 days.

(21) Appl. No.: 17/875,765

(22) Filed: Jul. 28, 2022

(65) Prior Publication Data

US 2023/0058304 A1 Feb. 23, 2023

(30) Foreign Application Priority Data

Aug. 3, 2021 (JP) ................................ 2021-127548

(51) Int. Cl.

*G01N 30/88* (2006.01)
*G01N 33/68* (2006.01)
*G01N 35/10* (2006.01)
*G01N 30/02* (2006.01)

(52) U.S. Cl.

CPC ......... *G01N 30/88* (2013.01); *G01N 33/6812* (2013.01); *G01N 35/1016* (2013.01); *G01N 2030/027* (2013.01); *G01N 2030/8804* (2013.01); *G01N 2030/8818* (2013.01)

(58) Field of Classification Search

None
See application file for complete search history.

(56) References Cited

FOREIGN PATENT DOCUMENTS

| | | |
|---|---|---|
| JP | 4291628 B2 | 7/2009 |
| JP | 2018-163155 A | 10/2018 |

OTHER PUBLICATIONS

Corleto, K. et al. A sensitive HPLC-FLD method combined with multivariate analysis for the determination of amino acids in L-citrulline rich vegetables, Journal of Food and Drug Analysis, 27, 717-728 (Year: 2019).*
Hans Bruckner et al., "Automated enantioseparation of amino acids by derivatization with o-phthaldialdehyde and n-acylated cysteines", J of Chromatography, 1989, pp. 73-82, vol. 476.

(Continued)

*Primary Examiner* — Xiaoyun R Xu
(74) *Attorney, Agent, or Firm* — Sughrue Mion, PLLC

(57) ABSTRACT

A method for analyzing amino acids by liquid chromatography, in which a sample containing a plurality of kinds of amino acids is derivatized with a derivatization reagent, and the obtained derivatized sample is circulated on a column together with a mobile phase. Two or more kinds of derivatized samples are prepared using two or more kinds of derivatization reagents. Different analytical conditions in which mixing ratio of the plurality of the mobile phases is changed with a passage of time are set for each kind of the derivatization reagent. A solvent mixing ratio in the mobile phase being the mixed solvent system is set for the each kind of the derivatization reagent. The two or more kinds of derivatized samples are analyzed by automatically switching between the different analytical conditions and the solvent mixing ratio to separate and quantify derivatized L-amino acids and derivatized D-amino acids.

10 Claims, 4 Drawing Sheets

(56) References Cited

OTHER PUBLICATIONS

"Development of a Simultaneous Analysis Technique for Trace D-Amino Acids for Use in Disease Diagnosis to Create New Drugs", NEDO (New Energy and Industrial Technology Development Organization), 2008, 5 pages News Release, Industrial Technology Subsidy vol. 14, URL:https://www.nedo.go.jp/news/press/AA5_0386A.html.

Kenji Hamase et al., "Comprehensive analysis of branched aliphatic D-amino acids in mammals using an integrated multi-loop two-dimensional column-switching high-performance liquid chromatographic system combining reversed-phase and enantioselective columns", Journal of Chromatography A, 2007, pp. 105-111, vol. 1143.

Wouter F. Visser et al., "A sensitive and simple ultra-high-performance-liquid chromatography- tandem mass spectrometry based method for the quantification of D-amino acids in body fluids", Journal of Chromatography A, 2011, pp. 7130-7136, vol. 1218.

Jun Zhe Min et al., "Determination of DL-amino acids, derivatized with R(−)-4-(3-isothiocyanatopyrrolidin-1-yl)-7-(N,N-dimethylaminosulfonyl)-2,1,3-benzoxadiazole, in nail of diabetic patients by UPLC-ESI-TOF-MS", Journal of Chromatography B, 2011, pp. 3220-3228, vol. 879.

Yosuke Nakano et al., "Development of a liquid chromatography-tandem mass spectrometry method for quantitative analysis of trace o-amino acids", Journal of Bioscience and Bioengineering, 2017, pp. 134-138, vol. 123, No. 1.

* cited by examiner

AMINO ACID ANALYSIS METHOD

TECHNICAL FIELD

The present invention relates to a method for analyzing amino acids. Specifically, the present invention relates to a method for simultaneous analysis of L-amino acids and D-amino acids constituting a protein.

RELATED ART

Most amino acids have an asymmetric carbon atom at α-position, and there are L-form and D-form enantiomers. Most of the amino acids existing in nature, including constituent units of proteins, are L-amino acids, but in recent years, it has become known that fermented foods and biological samples contain several kinds of D-amino acids in addition to many L-amino acids. A demand for D/L separation of amino acids is increasing in order to advance research on a role of D-amino acids in a body and in taste, preservability, aroma, etc. of foods and foodstuffs, and to use them for development of pharmaceuticals and functional foods. Since an amount of D-amino acid is smaller than that of L-amino acid in foods and in vivo, it is required to separate and quantify L-amino acids present in high concentration.

As a high performance liquid chromatograph (HPLC) analytical method for an amino acid containing a D-form (hereinafter, may be referred to as "D/L-amino acid"), a method of derivatizing with an optically active pre-column derivatization reagent and separating and detecting the L-form and D-form of amino acids on a reversed phase column (see Patent Document 1 and Non-Patent Document 1) is known.

Also, in general, when analyzing D/L-amino acids by HPLC, it is difficult to separate all the components under a single analytical condition. Therefore, as a method for performing simultaneous analysis of a plurality of amino acids, a method by two-dimensional HPLC has been proposed. For example, a method of detecting fluorescence or MS after derivatization using a reversed phase column and a chiral column (see Patent Document 2, Non-Patent Document 2 and Non-Patent Document 3), pre-column derivatized liquid chromatography/tandem mass spectrometry (LC-MS/MS method: see Non-Patent Document 4 and Non-Patent Document 5), and non-derivatized LC-MS/MS method in which two kinds of chiral columns are used alternately and the amino acids in the sample are detected by LC/MS without derivatization (see Non-Patent Document 6) have been reported.

PRIOR ART DOCUMENT

Patent Document

Patent Document 1: JP-A 2018-163155

Patent Document 2: Japanese Patent No. 4,291,628

Non-Patent Document

Non-Patent Document 1: Brueckner H., Wittner R., Godel H., J Chromatogr. A 1989; 476:73-82.

Non-Patent Document 2: New Energy and Industrial Technology Development Organization News Release, Industrial Technology Subsidy Vol. 14, Jul. 31, 2008, URL: https://www.nedo.go.jp/news/press/AA5_0386.html Non-Patent Document 3: Hamase K., Morikawa A., Ohgusu T., Lindner W., Zaitsu K., J. Chromatogr. A2007; 1143: 105-111.

Non-Patent Document 4: Visser W. F., Verhoeven-Duif N. M., Ophoff R., Bakker S., Klomp L. W., Berger R., et al. J. Chromatogr. A 2011; 1218:7130-6.

Non-Patent Document 5: Min J. Z., Hatanaka S., Yu H. F., Higashi T., Inagaki S., Toyo'oka T., J. Chromatogr. B Analyt. Technol. Biomed. Life Sci. 2011; 879:3220-8.

Non-Patent Document 6: Nakano Y., Konya Y., Taniguchi M., Fukusaki E., J. Biosci. Bioeng. 2017; 123:134-138.

SUMMARY OF THE INVENTION

Problem to be Solved by the Invention

The analytical method using a special derivatization reagent has a problem in application to simultaneous analysis of various D/L-amino acids from the viewpoint of cost and versatility.

The method by two-dimensional HPLC has a problem that the analysis requires a long time, and a complicated system is required. That is, when D/L-amino acids in a sample are simultaneously analyzed using a plurality of analytical conditions (mobile phase, column, etc.), it is necessary to replace the mobile phase when switching the analytical conditions, and in the case of completely different analytical conditions, it takes time not only to switch the mobile phase in a device but also to equilibrate the column to be used. In addition, it takes time and effort to prepare a mobile phase corresponding to each of a plurality of analytical conditions.

Furthermore, depending on the kind of D-amino acid to be analyzed, it is necessary to carry out two or more kinds of different derivatization reactions for one sample, and it takes time and effort to prepare two or more vials per sample, that is, twice or more the number of samples, and to perform derivatization reaction by humans.

On the other hand, LC/MS analysis requires an expensive system and is susceptible to the matrix effect that impurities contained in the sample cause ion suppression and enhancement with respect to a signal intensity when the target component is ionized and is less quantitative than other HPLC detectors. Therefore, when quantifying, it is necessary to correct by the internal standard. In addition, since an ion pair reagent (trifluoroacetic acid, etc.) that causes LC/MS contamination is used, it is necessary to specialize the device.

An object of the present invention is to provide a method for analyzing amino acids capable of easily analyzing D/L-amino acids in a sample with high reproducibility, and particularly to provide a simultaneous analytical method for L-amino acids and D-amino acids constituting a protein.

Means for Solving the Problem

The present invention has the following aspects.

[1] A method for analyzing amino acids by liquid chromatography, in which a sample containing a plurality of kinds of amino acids is derivatized with a derivatization reagent, and the obtained derivatized sample is circulated on a column together with a mobile phase, wherein the mobile phase is composed of a plurality of mobile phases, and at least one mobile phase is a mixed solvent system, wherein two or more kinds of derivatized samples are prepared using two or more kinds of derivatization reagents, wherein different analytical conditions in which mixing ratio of the plurality of the mobile phases is changed with a passage of time are set for each kind of the derivatization reagent, and a solvent mixing ratio in the mobile phase being the mixed solvent system is set for the each kind of the derivatization reagent, and wherein the two or more kinds of derivatized samples are analyzed by automatically switching between the different analytical conditions and the solvent mixing ratio to separate and quantify derivatized L-amino acids and derivatized D-amino acids.

[2] The method in the above-mentioned item (1), wherein aspartic acid, glutamic acid, asparagine, serine, glutamine, histidine, threonine, arginine, alanine, tyrosine, valine, methionine, cystine, tryptophan, isoleucine, phenylalanine, leucine, lysine, and glycine are analyzed as the amino acids.

[3] The method in the above-mentioned item (1) or (2), wherein the plurality of the mobile phases are composed of two kinds, mobile phase A and mobile phase B, and wherein for the each kind of the derivatization reagent, analytical conditions that change the mixing ratio of the mobile phase A and the mobile phase B with the passage of time are set, and the different analytical conditions are automatically switched to analyze the two or more kinds of derivatized samples.

[4] The method in the above-mentioned item (3), wherein the mobile phase A is a buffer solution, and the mobile phase B is a mixed solvent system.

[5] The method in the above-mentioned item (3) or (4), wherein the mobile phase B is the mixed solvent system of water, acetonitrile and methanol, and the solvent mixing ratio is set for the each kind of the derivatization reagent and is automatically switched for each analysis of the two or more kinds of derivatized samples.

[6] The method in the above-mentioned items (1) to (5), wherein two kinds of a mixture of o-phthalaldehyde and N-acetyl-L-cysteine and a mixture of o-phthalaldehyde and N-isobutyryl-L-cysteine are used as the derivatization reagent.

[7] The method in the above-mentioned items (1) to (6), wherein derivatization of the sample is performed by an automatic sample introduction device having a pretreatment function.

[8] The method in the above-mentioned items (1) to (7), wherein a pH of the mobile phase circulating in the column is 7-12.

Effects of the Invention

According to the present invention, it is possible to provide a method for analyzing amino acids capable of easily analyzing D/L-amino acids in a sample with high reproducibility, and particularly to provide a simultaneous analytical method for L-amino acids and D-amino acids constituting a protein.

MODE FOR CARRYING OUT THE INVENTION

Figure 1:
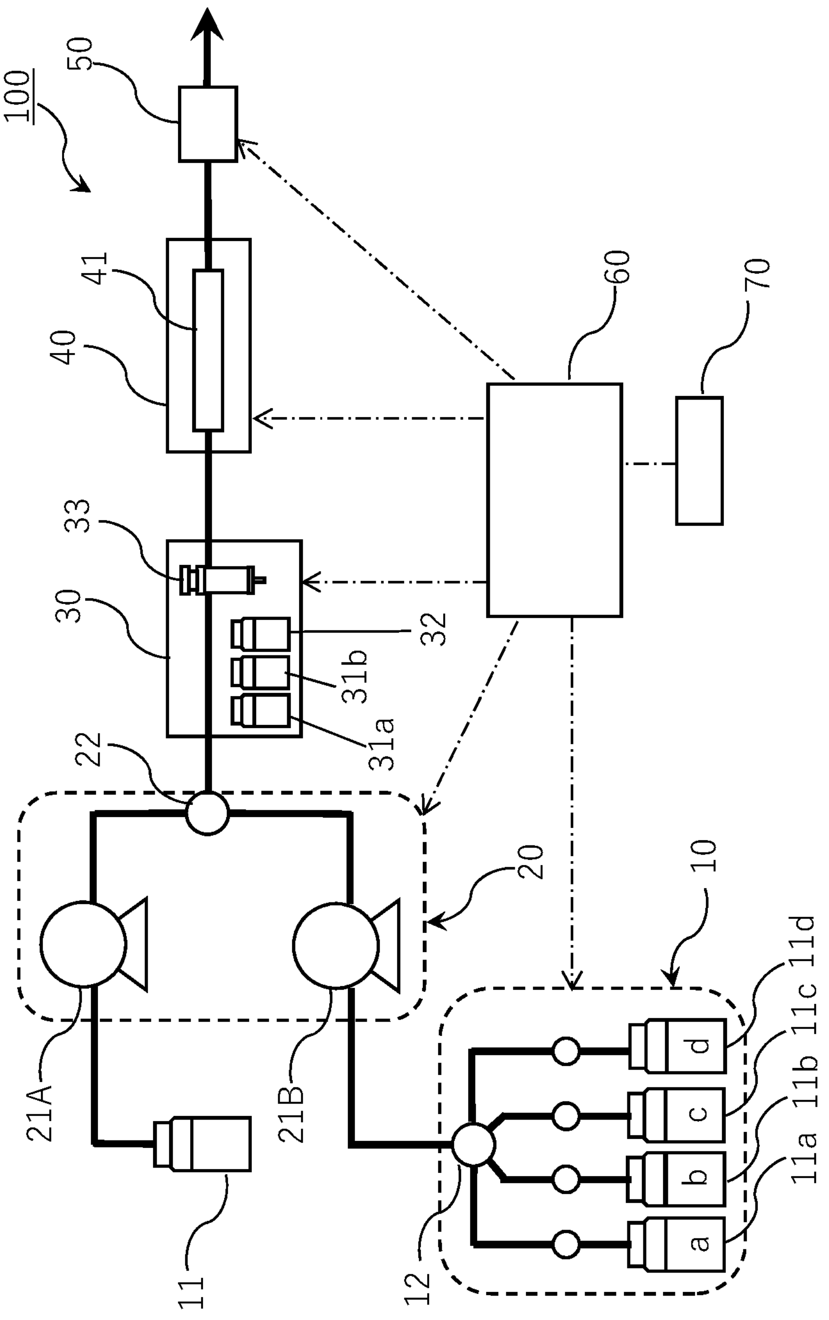
FIG. 1 is a schematic configuration diagram showing an example of a liquid chromatograph analysis system used in the method for analyzing amino acids according to the present invention.

The present invention is a method for analyzing amino acids (hereinafter, may be simply referred to as "the present method") by liquid chromatography, in which a sample containing a plurality of kinds of amino acids is derivatized with a derivatization reagent, and the obtained derivatized sample is circulated on a column together with a mobile phase, wherein the mobile phase is composed of a plurality of mobile phases, and at least one mobile phase is a mixed solvent system, wherein two or more kinds of derivatized samples are prepared using two or more kinds of derivatization reagents, wherein different analytical conditions in which mixing ratio of the plurality of the mobile phases is changed with a passage of time are set for each kind of the derivatization reagent, and a solvent mixing ratio in the mobile phase being the mixed solvent system is set for the each kind of the derivatization reagent, and wherein the two or more kinds of derivatized samples are analyzed by automatically switching between the different analytical conditions and the solvent mixing ratio to separate and quantify derivatized L-amino acids and derivatized D-amino acids.

The amino acids to be analyzed by the present method are preferably amino acids other than proline, which constitutes a protein. Specifically, examples of the amino acids to be analyzed include aspartic acid (Asp), glutamic acid (Glu), asparagine (Asn), serine (Ser), glutamine (Gln), histidine (His), threonine (Thr), arginine (Arg), alanine (Ala), tyrosine (Tyr), valine (Val), methionine (Met), cystine ($(Cys)_2$), tryptophan (Trp), isoleucine (Ile), phenylalanine (Phe), Leucine (Leu), lysine (Lys) and glycin (Gly). Among these amino acids, L-form and D-form exist in amino acids other than glycine, which does not have an asymmetric carbon atom in the molecule. That is, in the present method, it is possible to preferably analyze the amino acids of 37 components all at once.

In the present method, two or more kinds of derivatization reagents are used. As the amino acid derivatization reagents, compounds having a substituent that reacts with a free amino group to promote amino acid analysis have been conventionally used, and examples of the amino acid derivatization reagents include ninhydrin, phenyl isothiocyanate (PITC), o-phthalaldehyde (OPA), 2,4-dinitrofluorobenzene (DNFB), Nα-(2,4-dinitro-5-fluorophenyl)-L-alanine amide (FDAA), 4-fluoro-7-nitrobenzoflazan (NBD-F) and the like.

In the present method, the derivatization reagent derivatizes a D/L-amino acid as a diastereomer, and the derivatized D-amino acid and the derivatized L-amino acid can be analyzed by fluorescence detection. As such derivatization reagents, it is highly preferable to use two kinds of a mixture of OPA and N-acetyl-L-cysteine (NAC) (hereinafter, sometimes referred to as "OPA/NAC"), and OPA and N-isobutyryl-L-cysteine (NIBC) (Hereinafter, sometimes referred to as "OPA/NIBC"), it is extremely preferable to use two kinds.

Both NAC and NIBC are chiral thiols having optically active sites, and the D/L-amino acid can be converted into diastereomeric fluorescent derivatives by reacting OPA in the presence of these chiral thiols and can be analyzed by fluorescence detection.

In the present method, derivatization treatment of the sample to be analyzed may be manually performed in advance, and a plurality of derivatized samples may be prepared and analyzed. However, from the viewpoint of more efficiently performing the present method, it is preferable to perform the derivatization treatment with an automatic sample introduction device having a pretreatment function (hereinafter, also referred to as an autosampler).

When the autosampler with the pretreatment function is used, by setting a vial containing the derivatization reagent and the sample to be analyzed in the autosampler in which an operation of automatically mixing the derivatization reagent and the sample for derivatization is programmed and executing the above setting, the derivatization treatment can be performed automatically and the derivatized sample can be used for analysis as it is.

The derivatization treatment with the autosampler may be performed in a vial, or the derivatization treatment may be performed in a needle if it has a function of mixing in the needle.

The sample containing a plurality of kinds of amino acids is derivatized with a derivatization reagent, and the obtained derivatized sample is circulated on a column together with a mobile phase for analysis by HPLC.

An average particle size of a packing material of the column is preferably 1 to 6 μm, may have fine pores, and may be particles having a specific surface area of 50 to 600 $m^2/g$, for example, silica particles. Such particles may have a bonded surface that interacts with the derivatized amino acids to facilitate the separation of the amino acids. Suitable bonded surfaces include hydrophobic bonded surfaces such as, for example, alkyl bonded surfaces which may contain C4, C8 or C18 alkyl bond groups. More specifically, examples of the column include a column using silica particles whose surface is modified with an octadecylsilyl (ODS) group as a filler (stationary phase).

A length of the column is preferably in the range of 15 to 300 mm, and a diameter is preferably in the range of 0.5 to 5 mm. Commercially available products can be used as the column, and examples of suitable columns include Sim-pack Scepter (registered trademark).

In the present method, the mobile phase is composed of a plurality of mobile phases, and at least one mobile phase is a mixed solvent system, and HPLC analysis is performed while changing composition of the plurality of the mobile phases (hereinafter, also referred to as gradient conditions). Specifically, the analysis is started with hydrophilicity of the mobile phase circulating through the column being high, and the gradient condition is set so that the hydrophilicity of the mobile phase is gradually lowered (an amount of hydrophobic solvent in the mobile phase is increased) with the passage of time. By changing the hydrophilicity of the mobile phase in this way, the hydrophilic amino acids are eluted through the column before the hydrophobic amino acids and compared with isocratic conditions that do not change the composition of the mobile phase, the time required for analysis can be shortened, and various amino acids can be analyzed all at once with high reproducibility.

When analyzing the derivatized sample by adding multiple derivatization reagents to the target sample by the conventional D-amino acid analytical method, first, the sample derivatized with one of the derivatization reagents is analyzed by HPLC, and then the sample derivatized with another derivatizing reagent is analyzed by HPLC. At this time, various analytical conditions such as the mobile phase, the column type, and the initial conditions of the gradient conditions are often significantly changed, which takes time and effort. In addition, a cost of various consumer goods used for analysis, such as preparation of the mobile phases corresponding to a plurality of the analytical conditions and preparation of vials having a volume of twice or more the number of samples, could not be ignored.

In a preferred embodiment of the present method, the plurality of the mobile phases comprises two kinds, mobile phase A and mobile phase B, and the analytical conditions for changing a mixing ratio of the mobile phase A and the mobile phase B with the passage of time are set for each kind of the derivatization reagent. Preferably, the mobile phase A is a buffer solution, the mobile phase B is a mixed solvent system, and a solvent mixing ratio in the mobile phase B is set for each kind of derivatization reagent.

Further, when the OPA/NAC and the OPA/NIBC described above are used as the two or more kinds of derivatization reagents, the solvent species of the mixed solvent system constituting the mobile phase A and the mobile phase B in the analysis of the two kinds of derivatized samples can be the same. Then, the conditions other than the gradient conditions of the mobile phase A and the mobile phase B and the mixed solvent ratio of the mixed solvent system of the mobile phase B, that is, the column type, a column temperature, a flow velocity of the mobile phase, the analytical conditions of the detector and the like can be the same.

Therefore, by automatically switching only the different analytical conditions, the two or more kinds of derivatized samples can be easily analyzed, and the derivatized L-amino acid and the derivatized D-amino acid can be separated and quantified with high reproducibility.

Examples of the buffer solution that can be used for the mobile phase A include an acetic acid-based buffer solution, a phosphoric acid-based buffer solution, a boric acid-based buffer solution and the like. Among them, a pH of the mobile phase A is preferably 5 or more, and more preferably in the range of 7 to 12, and particularly preferably in the range of 7 to 11. Further, it is preferable that the buffer solution can maintain the pH in the range of 7 to 12, and preferably in the range of 7 to 11 after the mobile phase A and the mobile phase B are mixed, and a phosphoric acid-based buffer solution is more preferable.

The buffer solution may contain an inorganic salt, a bacteriostatic agent, a surfactant and the like as long as accuracy of the amino acid analysis in the present method is not impaired.

Examples of the solvent constituting the mixed solvent system that can be used for the mobile phase B include water, acetonitrile, methanol, ethanol, isopropanol, tetrahydrofuran and the like. These may be a mixture of two kinds or a mixture of three or more kinds.

Among them, it is preferable that the mobile phase B is the mixed solvent system of water, acetonitrile and methanol. Moreover, it is preferable to set the solvent mixing ratio for each kind of the derivatization reagent. In such an embodiment, the solvent mixing ratio may be automatically switched for each analysis of the two or more kinds of derivatized samples, which is preferable.

A particularly preferred embodiment of the present method sets the mobile phase as follows.

That is, in the analysis of the sample derivatized by OPA/NAC, a selection of the solvent kind of the mixed solvent system in the mobile phase B and a blending amount ratio are set to water/acetonitrile/methanol=15/10/75 (volume ratio). In the analysis of the sample derivatized by OPA/NIBC, the mixed solvent system in mobile phase B is water/acetonitrile/methanol=10/20/70 (volume ratio).

Compared to the OPA/NAC analysis, the mobile phase B in the OPA/NIBC analysis has a low water content and a high acetonitrile content and is relatively hydrophobic. Further, while NAC has an acetyl group, NIBC has an isobutyryl group, so that it is relatively hydrophobic. By utilizing this difference in hydrophobicity, it is possible to simultaneously analyze a plurality of amino acids, specifically protein-constituting D/L-amino acids, including glycine.

Hereinafter, the present method will be described in detail with reference to the drawings.

1. Configuration of Liquid Chromatograph Analysis System

FIG. 1 is a schematic configuration diagram of an example of a liquid chromatograph analysis system for carrying out the present method. The liquid chromatograph analysis system 100 includes a mobile phase blending unit 10, a liquid feeding unit 20, an autosampler 30, a column oven 40 and a column 41, a detector 50, a control unit 60, and a display unit 70. The liquid chromatograph analysis system 100 is not limited to these configurations, and any other configuration may be added or replaced with any configuration that exhibits the same function.

The liquid feeding unit 20 has a liquid feeding pump that sucks and feeds the plurality of the mobile phases, and a mixer that mixes the plurality of the mobile phases at a predetermined mixing ratio. FIG. 1 shows an example in which liquid feeding pumps 21A and 21B for feeding two kinds of the mobile phases (the mobile phase A and the mobile phase B) are provided, and a mobile phase container 11 in which the mobile phase A is stored is connected to the liquid feeding pump 21A, and a mobile phase blending unit 10 is connected to the liquid feed pump 21B. Further, a mixer 22 for mixing the mobile phase A and the mobile phase B, which are fed from the liquid feeding pumps 21A and 21B, respectively, at a predetermined mixing ratio is provided.

The mobile phase blending unit 10 has mobile phase containers in which a plurality of different mobile phases are stored, and FIG. 1 shows an example including mobile phase containers 11*a*, 11*b*, 11*c* and 11*d* in which four mobile phases (hereinafter, referred to as solvent a, solvent b, solvent c, and solvent d) are stored.

The mobile phase blending unit 10 includes a mixer 12 including a plurality of open-adjustable solenoid valves that suck solvent a, solvent b, solvent c and solvent d from the mobile phase containers 11*a*, 11*b*, 11*c* and 11*d* and mix them at a predetermined mixing ratio to prepare mobile phase B, and the prepared mobile phase B is fed by a liquid feed pump 21B.

The autosampler 30 includes an autoinjector 33 that injects a fixed amount of sample. The autosampler 30 preferably has a pretreatment function for an analysis sample, and a plurality of derivatizing reagents 31*a* and 31*b* and an analysis sample 32 can be provided.

A mobile phase in which the mobile phase A and the mobile phase B are mixed at a predetermined mixing ratio is sent to the autosampler 30 via the mixer 22. Using the pretreatment function of the autosampler 30, the derivatization reagent and the analysis sample are mixed in advance for derivatization treatment, and the prepared derivatized sample is sucked by an autoinjector 33 in a predetermined amount and injected into the mobile phase. The derivatized sample injected by the autoinjector 33 passes through the column 41 that separates the derivatized amino acid component in the time direction together with the mixed mobile phase, and the separated derivatized amino acid component contained in the sample is detected by the vessel 50. The column oven 40 keeps the column 41 at a constant temperature during the analysis. The column 41 is, for example, a reversed phase column (such as a C18 column having silica gel whose surface is modified with an ODS (octadecylsilyl) group as a stationary phase).

The detector 50 is a fluorescence detector, which fluoresces by exciting a derivatized amino acid component in a sample with excitation light having a specific excitation wavelength and detects fluorescence having a specific fluorescence wavelength.

The control unit 60 is electrically connected to the mobile phase blending unit 10, the liquid feeding unit 20, the autosampler 30, the column oven 40 and the detector 50, and has a function of controlling these operations based on the set analytical conditions and a function of performing predetermined arithmetic processing (creating a chromatogram and the like) based on the detection signal. In the embodiment of the present method, the analysis is performed while changing the mixing ratio of the plurality of mobile phases with the passage of time in the mixer 22.

In the control unit 60, a plurality of analytical conditions can be set for each kind of the plurality of derivatization reagents used in the present method. The analytical conditions include, for example, the kind of sample, the kind of the mobile phase, the type of column and the like. As a result, the liquid chromatograph analysis system 100 can analyze the sample under a plurality of the analytical conditions.

The control unit 60 has a built-in storage unit, and the storage unit is composed of, for example, a ROM containing operation programs required for control of CPU that executes logical operations, mobile phase blending unit 10, liquid feeding unit 20 and the like, a RAM in which data and the like are temporarily stored during control, and the like.

The CPU or the like included in the control unit 60 appropriately controls each part of the mobile phase blending unit 10, the liquid feeding unit 20, and the pretreatment of the autosampler 30 according to the operation programs, so that the analysis operation described later is performed. The data detected by the detector 50 is processed by the control unit 60 to identify and quantify the amino acid components in the sample. Further, the display unit 70 is, for example, a liquid crystal display and displays an analysis result or the like.

The control unit 60 can realize each function by using a personal computer or a more advanced workstation as a hardware resource and executing dedicated control/processing software pre-installed in the computer on the computer, so that the entire liquid chromatograph analysis system 100 can be controlled.

2. Analysis Operation

Next, the analysis operation using the liquid chromatograph analysis system of FIG. 1 will be described with reference to the flowchart of FIG. 2.

The analysis sample and the plurality of the derivatization reagents (OPA/NAC as the derivatization reagent 1 and OPA/NIBC as the derivatization reagent 2) are provided in the automatic sample introduction device (autosampler 30) having a pretreatment function.

The control unit 60 controls the mobile phase B to a solvent mixing ratio condition 1, controls the liquid feeding pumps 21A and 21B so that the mobile phase A and the mobile phase B have a predetermined initial mixing ratio under the gradient condition 1, and operates the liquid feeding pumps 21A and 21B so that the mixed mobile phase has a predetermined flow rate.

Here, in the examples described later, the mobile phase container 11 in which the phosphoric acid-based buffer solution is stored as the mobile phase A and the three mobile phase containers 11*a*, 11*b* and 11*c* in which water, acetonitrile and methanol are stored, respectively (the mobile phase container 11*d* is unused). The control unit 60 controls the mixer 12 of the mobile phase blending unit 10 to mix water, acetonitrile and methanol under the preset solvent mixing ratio condition 1 to prepare the mobile phase B. Then, the mobile phase A is fed by the liquid feeding pump 21A, and the mobile phase B is fed by the liquid feed pump 21B, respectively, and in the mixer 22, the mobile phase mixed at the predetermined initial mixing ratio under the gradient condition 1 is flowed through the autosampler 30 to the column 41 at a constant flow rate.

Both the solvent mixing ratio condition 1 of water, acetonitrile and methanol in the mobile phase B and the gradient condition 1 of the mobile phase A and the mobile phase B are conditions set corresponding to the analysis of the derivatized sample 1 derivatized by the derivatizing reagent 1.

Next, the autosampler 30 is controlled according to the operation program stored in the control unit 60 in advance, and the analysis sample is derivatized with the derivatizing reagent 1 to prepare the derivatized sample 1.

The derivatization treatment can be performed by weighing and mixing a predetermined amount of the derivatization reagent and the analysis sample in another vial (not shown) placed in the autosampler 30. Alternatively, when the autosampler 30 has a pretreatment function capable of continuously sucking a predetermined amount of the derivatization reagent and the analysis sample into the needle of the autoinjector 33 and mixing them in the needle, the derivatization treatment can also be performed by mixing the derivatization reagent and the analysis sample using such a function.

The derivatized sample may be provided in the autosampler 30 after the derivatization treatment of the analysis sample is manually performed in advance, but by using the pretreatment function of the autosampler 30 to provide the derivatization reagent and the analysis sample in advance and control the derivatization treatment automatically, labor and time required for the pretreatment can be reduced. In addition, the constant reaction time of derivatization improves stability and reproducibility.

When the control unit 60 instructs to start the analysis of the derivatized sample 1, the autoinjector 33 provided in the autosampler 30 injects a predetermined amount of the derivatized sample 1 into the mobile phase at a predetermined timing in response to the instruction. The injected derivatized sample 1 is introduced into the column 41 along with the flow of the mobile phase, and while passing through the column 41, the derivatized amino acid component in the sample is separated in the time direction and eluted from the outlet of the column 41.

The control unit 60 also changes the mixing ratio of the mobile phase A and the mobile phase B in the mixer 22 over time according to the gradient condition 1 from the time of injecting the derivatized sample 1. That is, during the analysis, the control unit 60 supplies the column 41 as a mobile phase while increasing the mixing ratio of the mobile phase B containing the organic solvent with the passage of time. The control unit 60 may have a gradient time program creation unit configured to execute the gradient condition 1 of the mobile phase A and the mobile phase B.

A detection signal from the detector 50 is acquired by the control unit 60 controlling the operation of each unit based on the analysis control program set in advance.

After the last component of the 37 amino acids has been eluted, the mixing ratio of the mobile phase A and the mobile phase B is returned to the initial ratio by the gradient condition 1, a sufficient equilibration time is secured, and the analysis of the derivatized sample 1 is completed.

When there are a plurality of derivatized samples 1 to be analyzed by providing the plurality of analysis samples in the autosampler 30, the control unit 60 instructs the start of analysis of the subsequent derivatized sample 1 after the analysis of the previous derivatized sample 1 is completed, the mixing ratio of mobile phase A and mobile phase B returns to the initial ratio, and the above equilibration time elapses. Then, the liquid feeding pumps 21A and 21B are controlled so that the mobile phase A and the mobile phase B have a predetermined initial mixing ratio under the gradient condition 1, the liquid feeding pumps 21A and 21B are operated so that the mixed mobile phase has a predetermined flow rate, and then the last component of the 37 amino acids has been eluted, the mixing ratio of the mobile phase A and the mobile phase B is returned to the initial ratio by the gradient condition 1, and the equilibration time is sufficiently secured repeatedly.

After the analysis of the derivatized sample 1 is completed, the solvent mixing ratio conditions are changed. That is, the control unit 60 adjusts the mixing amount ratio of water, acetonitrile and methanol in the mixer 12 of the mobile phase blending unit 10 to adjust the solenoid valve from each mobile phase container. Thereby, the control unit 60 controls to prepare the mobile phase B by changing from the solvent mixing ratio condition 1 to the solvent mixing ratio condition 2. Then, the mobile phase A is fed by the liquid feeding pump 21A and the mobile phase B is fed by the liquid feed pump 21B, and in the mixer 22, the mobile phase mixed at the predetermined initial mixing ratio under the gradient condition 2 is flowed through the autosampler 30 to the column 41 at a constant flow rate.

Here, the solvent mixing ratio condition 2 of water, acetonitrile and methanol in the mobile phase B and the gradient condition 2 of the mobile phase A and the mobile phase B are both conditions set corresponding to the analysis of the derivatized sample 2 derivatized by the derivatizing reagent 2.

Figure 2:
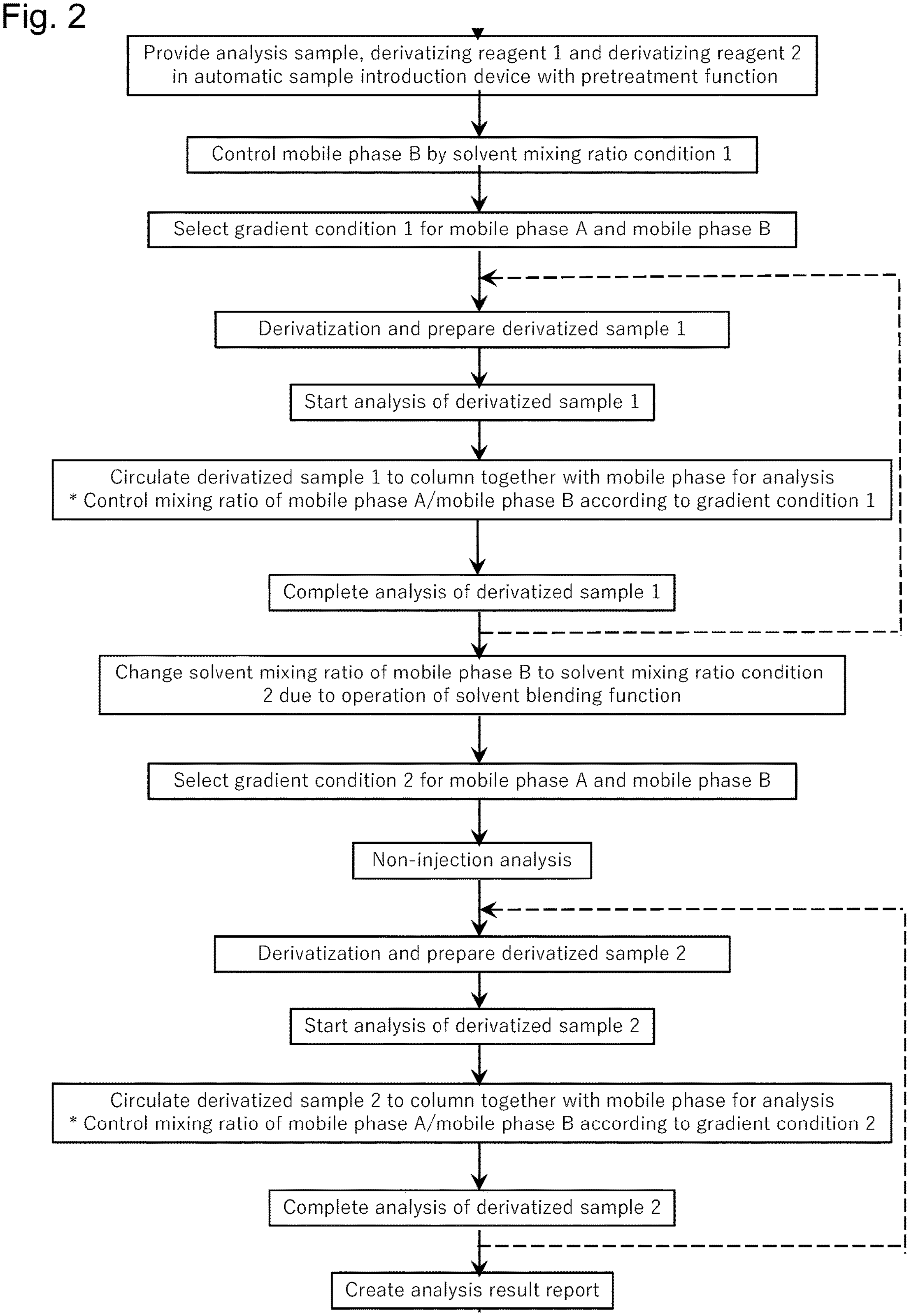
FIG. 2 is a flowchart of an analysis operation example using the liquid chromatograph analysis system of FIG. 1.

Then, it is preferable to perform a "non-injection analysis" in the flowchart of FIG. 2. Specifically, the control unit 60 changes the mixing ratio of the mobile phase A and the mobile phase B in the mixer 22 with the passage of time according to the gradient condition 2 prior to the analysis of the derivatized sample 2. After that, the control unit 60 performs an operation of supplying the mobile phase to the column 41 while executing the gradient condition 2.

After the "non-injection analysis" is completed, the autosampler 30 is controlled according to the operation program stored in advance in the control unit 60 to derivatize the analysis sample with the derivatizing reagent 2 to prepare the derivatized sample 2. The derivatization treatment can be performed in the same manner as described above. Subsequently, the start of analysis of the derivatized sample 2 is instructed.

In response to an instruction from the control unit 60, the autoinjector 33 provided in the autosampler 30 injects a predetermined amount of the derivatized sample 2 into the mobile phase at a predetermined timing. The injected derivatized sample 2 is introduced into the column 41 along with the flow of the mobile phase, and while passing through the column 41, the derivatized amino acid component in the sample is separated in the time direction and eluted from the outlet of the column 41.

From the time of injecting the derivatized sample 2, the control unit 60 changes the mixing ratio of the mobile phase A and the mobile phase B in the mixer 22 with the passage of time according to the gradient condition 2. After that, the mobile phase is supplied to the column 41 while executing the gradient condition 2. During the analysis, the control unit 60 controls the operation of each unit based on the analysis control program set in advance, so that the detection signal from the detector 50 is acquired.

After the last component of the 37 amino acid components has been eluted, the mixing ratio of mobile phase A and mobile phase B is returned to the initial ratio under gradient condition 2 and an equilibration time is sufficiently secured, and the analysis of the derivatized sample 2 is completed.

When there are a plurality of derivatized samples 2 to be analyzed by providing the plurality of analysis samples in the autosampler 30, the control unit 60 instructs the start of analysis of the subsequent derivatized sample 2 after the analysis of the previous derivatized sample 2 is completed, the mixing ratio of mobile phase A and mobile phase B returns to the initial ratio, and the above equilibration time elapses. Then, the liquid feeding pumps 21A and 21B are controlled so that the mobile phase A and the mobile phase B have a predetermined initial mixing ratio under the gradient condition 2, the liquid feeding pumps 21A and 21B are operated so that the mixed mobile phase has a predetermined flow rate, and then the last component of the 37 amino acids has been eluted, the mixing ratio of the mobile phase A and the mobile phase B is returned to the initial ratio by the gradient condition 2, and the equilibration time is sufficiently secured repeatedly.

The control unit 60 creates a chromatogram using the obtained data, calculates an area value of the peak on the chromatogram for the amino acids confirmed to be present in the sample, obtains a concentration value for each amino acid from the peak area value with reference to a calibration curve prepared in advance, and creates an analysis result report. The control unit 60 can have a data processing unit that creates the analysis result report.

After all the analysis is completed, a mixed solution of water and an organic solvent can be sent from the mobile phase blending unit 10 via the liquid feed pump 21B, and the system, column and the like can be washed as a post-treatment. By such post-treatment, it is possible to prevent the sample from remaining on the probe into which the sample is injected and precipitation of salt in the system and the column.

In the present method, each sample to be analyzed is derivatized using two kinds of derivatization reagents, and by examining the mobile phase selection and gradient conditions in the analysis of one derivatized sample and the other derivatized sample, it was possible to achieve most of the commonality between the first and second analytical conditions. Therefore, by simply changing and controlling the mixing ratio of the mixed solvent system of the mobile phase B and the gradient conditions of the mobile phase A and the mobile phase B under both analytical conditions, it enhances the separation performance of D-amino acids, which was difficult to separate and detect in the past and enables rapid simultaneous analysis of various amino acids.

An example of the controllable system described above is the Nexera (registered trademark) X3 system (manufactured by Shimadzu Corporation). This system is provided with a low pressure gradient kit, and a low pressure gradient unit in the kit corresponds to the mobile phase blending unit described above and has the mobile phase blending function capable of controlling the mixing ratio of a plurality of mobile phases. Since an analysis schedule with changed mobile phases and gradient conditions can be automatically created and switched by using the mobile phase blending function and the automatic preprocessing function of the autosampler, it is possible to reduce the time required for the preparation of the mobile phase and the replacement of the mobile phase, the labor for derivatization, and the like.

This method can be applied to amino acid content analysis in various fields such as biochemistry and medical fields, as well as analysis of alcoholic beverages and various foods. Examples of alcoholic beverages include beer, rice wine, red wine, white wine and other brewed alcoholic beverages. Examples of foods include fermented foods.

EXAMPLES

Hereinafter, the present invention will be specifically described with reference to examples, but the present invention is not limited to these examples.

[Preparation Example of Derivatization Reagent]

0.1 mol/l Boric Acid Buffer:

0.1 mol/l boric acid buffer was prepared by adding 0.62 g of boric acid and 0.20 g of sodium hydroxide to 100 ml of pure water and completely dissolving them.

O-Phthalaldehyde (OPA) Reagent:

O-phthalaldehyde (OPA) reagent was prepared by adding 0.3 ml of ethanol to 10 mg of OPA to completely dissolve it, and then adding 0.7 ml of 0.1 mol/l boric acid buffer and 4 ml of pure water.

N-Acetyl-L-Cysteine (NAC) Solution:

N-Acetyl-L-cysteine (NAC) solution was prepared by adding 10 ml of 0.1 mol/l boric acid buffer to 20 mg of NAC.

N-Isobutyryl-L-Cysteine (NIBC) Solution:

N-isobutyryl-L-cysteine (NIBC) solution was prepared by adding 10 ml of 0.1 mol/l boric acid buffer to 20 mg of NIBC.

<Derivatization Reagent 1: OPA/NAC>

The OPA reagent and the NAC solution were mixed in equal volumes and prepared and used for analysis.

<Derivatization Reagent 2: OPA/NIBC>

The OPA reagent and NIBC solution were mixed in equal volumes and prepared and used for analysis.

[Example of Preparation and Injection of Derivatized Sample by Autosampler]

4 μL of the derivatization reagent 1 or the derivatization reagent 2 was sucked into the needle of the autosampler, then 1 μL of the sample was sucked into the needle. These were mixed in the needle and then injected into the mobile phase.

The derivatization program can set the analysis sample, vial number, injection amount, mixing frequency, mixing capacity, waiting time, and air gap amount.

[Analysis Equipment]

HPLC system: Nexera X3 (manufactured by Shimadzu Corporation)
Degasser: DGU-403, DGU-405
Pump: LC-40D X3 (2 units), low pressure gradient kit (1 unit)
Autosampler: SIL-40C X3
Column constant temperature bath: CTO-40C
Communication bus module: SCL-40
Spectral fluorescence detector: RF-20AXS

[HPLC Analytical Conditions]

<<Derivatized Sample 1 Using Derivatization Reagent 1>>

Column: Sim-pack Scepter (registered trademark; manufactured by Shimadzu Corporation), Fixed phase C8, length 150 mm×inner diameter 3.0 mm, filling particle diameter 1.9 μm Mobile Phase:

[Mobile Phase A] A phosphoric acid-based buffer (10 mmol/L, pH 7.5) prepared by adding 0.68 g of potassium dihydrogen phosphate and 2.61 g of dipotassium hydrogen phosphate to 2000 mL of pure water and completely dissolving them.

[Mobile phase B] Water/acetonitrile/methanol=15/10/75

<Gradient Condition of Mobile Phase (Time Program)>

4% B (0-3 minutes)→11% B (13 minutes)→14% B (22 minutes)→25% B (30 minutes)→30% B (35 minutes)→41% B (61 minutes)→80% B (61.01-63 minutes)→4% B (63.01-67 minutes)

<Flow Velocity> 0.6 mL/min

Column temperature: 35° C.

Sample injection volume: 1 μL

Vial: SHIMADZU LabTotal (registered trademark) for LC 1.5 mL, Glass detector (FL): RF-20AXS, Ex: 350 nm, Em: 450 nm <<Derivatized Sample 2 Using Derivatization Reagent 2>>

Column: Sim-pack Scepter (registered trademark; manufactured by Shimadzu Corporation), Fixed phase C8, length 150 mm×inner diameter 3.0 mm, filling particle diameter 1.9 μm Mobile Phase:

[Mobile Phase A] A phosphoric acid-based buffer (10 mmol/L, pH 7.5) prepared by adding 0.68 g of potassium dihydrogen phosphate and 2.61 g of dipotassium hydrogen phosphate to 2000 mL of pure water and completely dissolving them.

[Mobile phase B] Water/acetonitrile/methanol=10/20/70

<Gradient Condition of Mobile Phase (Time Program)>

10% B (0 minutes) 15% B (3-15 minutes) 20% B (25 minutes)→52% B (57 minutes)→80% B (57.01-59 minutes)→10% B (59.01-63 minutes)

<Flow Velocity>0.6 mL/min

Column temperature: 35° C.

Sample injection volume: 1 μL

Vial: SHIMADZU LabTotal (registered trademark) for LC 1.5 mL, Glass detector (FL): RF-20AXS, Ex: 350 nm, Em: 450 nm

Example 1

By reacting the sample to be analyzed with the derivatizing reagent 1 (OPA/NAC) or the derivatizing reagent 2 (OPA/NIBC), the D/L-amino acids in the sample was diastereomeric fluorescently derivatized, and the derivatized sample was analyzed by HPLC under the above analytical conditions, and fluorescence was detected. Derivatization was performed automatically by the autosampler, and the mobile phase B was prepared using the mobile phase blending function of the liquid feed pump. After the analysis of the derivatized sample 1 was completed, the analytical condition was automatically switched to the derivatized sample 2.

Figure 3:
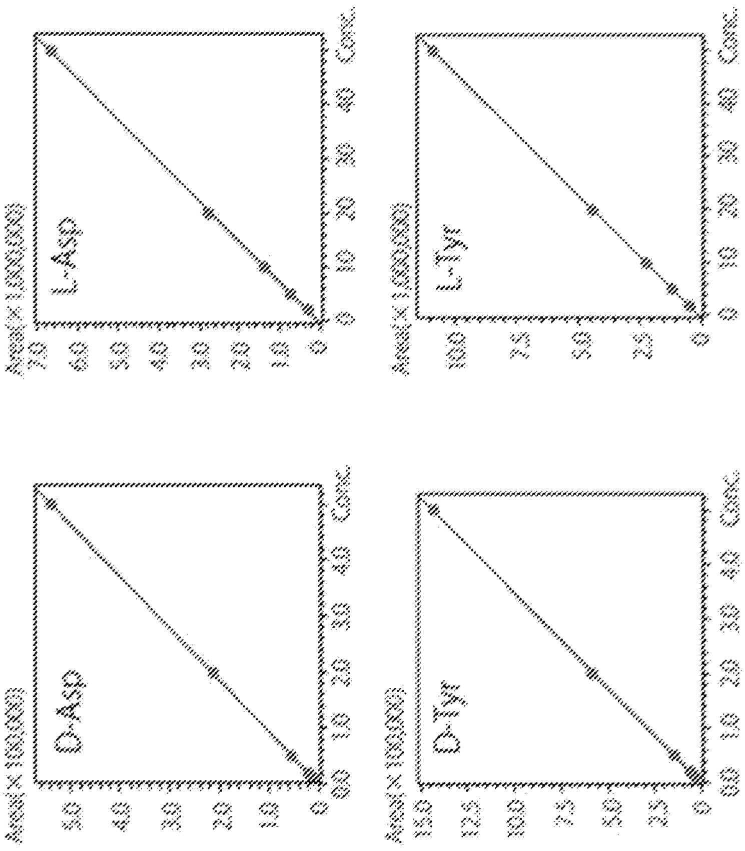
FIG. 3 is an example of a calibration curve obtained in the example.

2. Evaluation of Stability and Accuracy of Analytical Methods 2-1. Linearity of Calibration Curve By using two kinds of derivatization reagents, that is, different chiral thiols, 37 components of amino acids were separated. As for linearity of the calibration curve, the contribution rate (r2) was 0.999 or more. Table 1 shows the evaluation results of the linearity of the calibration curve for the amino acids of 37 components. An example of the obtained calibration curve is shown in FIG. 3.

TABLE 1

| | アミノ酸種 | 濃度範囲 (μmol/L) | 寄与率 ($r^2$) | | アミノ酸種 | 濃度範囲 (umol/L) | 寄与率 ($r^2$) |
|---|---|---|---|---|---|---|---|
| 1 | D-Asp | 0.1-5 | 0.99997 | 19 | L-Asp | 2-50 | 0.99968 |
| 2 | D-Glu | 0.1-5 | 0.99986 | 20 | L-Glu | 2-50 | 0.99999 |
| 3 | D-Asn | 0.1-5 | 0.99992 | 21 | L-Asn | 2-50 | 0.99999 |
| 4 | D-Ser | 0.1-5 | 0.99997 | 22 | L-Ser | 0.5-20 | 0.99996 |
| 5 | D-Gln | 0.1-5 | 0.99997 | 23 | L-Gln | 0.5-20 | 0.99995 |
| 6 | D-His | 0.2-50 | 0.99995 | 24 | L-His | 0.2-100 | 0.99991 |
| 7 | D-Thr | 0.1-5 | 1.00000 | 25 | L-Thr | 0.1-10 | 0.99957 |
| | | | | 26 | Gly | 0.5-100 | 0.99996 |
| 8 | D-Arg | 0.1-20 | 0.99994 | 27 | L-Arg | 2-100 | 0.99993 |
| 9 | D-Ala | 0.1-5 | 0.99997 | 28 | L-Ala | 5-100 | 0.99951 |
| 10 | D-Tyr | 0.1-5 | 0.99993 | 29 | L-Tyr | 2-50 | 0.99998 |
| 11 | D-Val | 0.1-2 | 1.00000 | 30 | L-Val | 2-50 | 0.99998 |
| 12 | D-Met | 0.1-5 | 0.99999 | 31 | L-Met | 0.1-5 | 0.99999 |
| 13 | D-$(Cys)_2$ | 0.1-5 | 0.99993 | 32 | L-$(Cys)_2$ | 2-50 | 0.99995 |
| 14 | D-Trp | 0.1-5 | 0.99996 | 33 | L-Trp | 2-50 | 0.99994 |
| 15 | D-Ile | 0.1-5 | 0.99990 | 34 | L-Ile | 0.5-20 | 0.99987 |
| 16 | D-Phe | 0.1-5 | 0.99997 | 35 | L-Phe | 2-50 | 0.99991 |
| 17 | D-Leu | 0.1-5 | 0.99996 | 36 | L-Leu | 2-50 | 0.99999 |
| 18 | D-Lys | 0.1-5 | 0.99996 | 37 | L-Lys | 0.5-20 | 0.99993 |

*斜体*:OPA/NAC*誘導体化*
常体:OPA/NIBC誘導体化

2-2. Reproducibility of Retention Time and Area of Each Amino Acid

Figure 4:
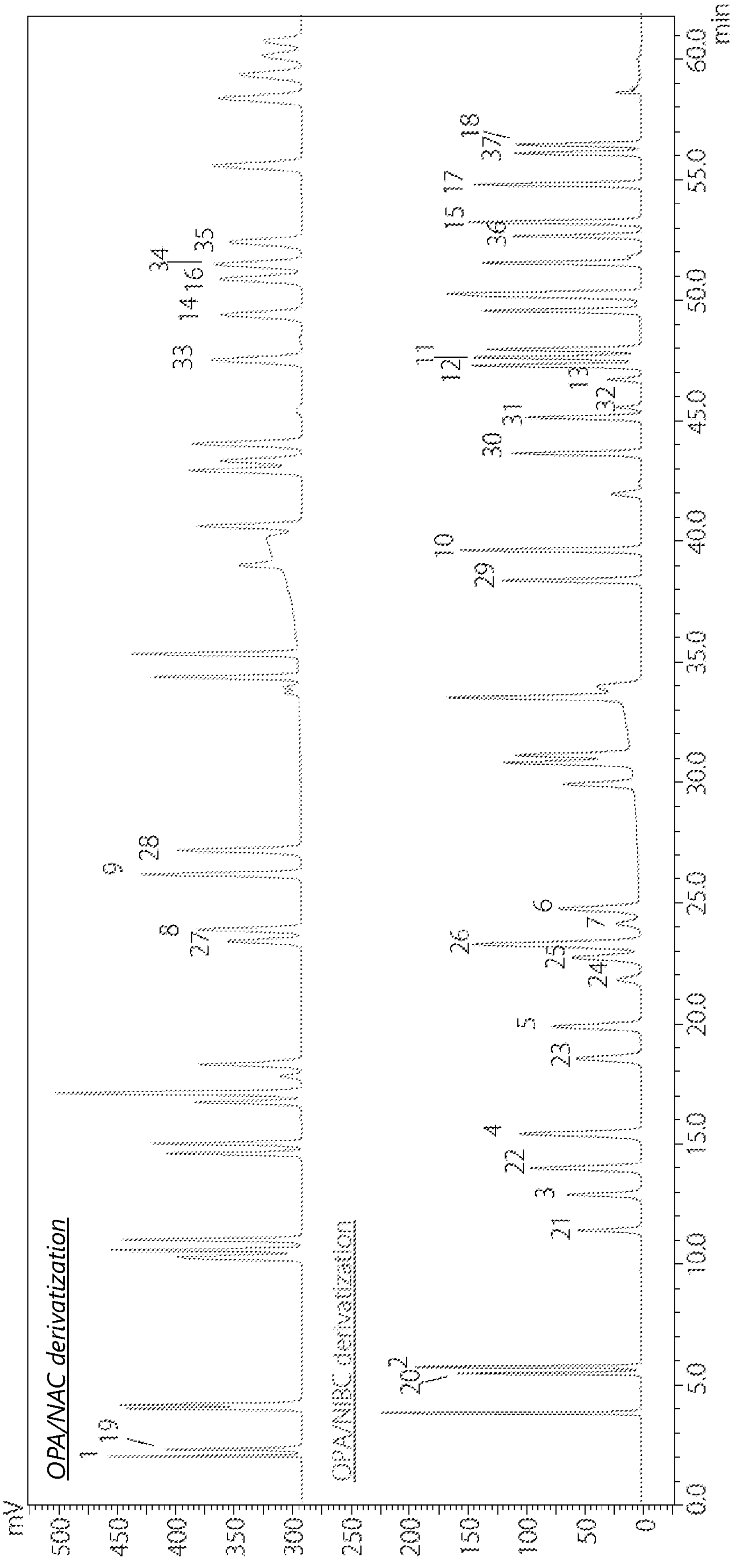
FIG. 4 is an example of a chromatogram obtained by measuring a standard sample of amino acids in an example.

When a retention time and area reproducibility (% RSD) of D/L-amino acid standard solutions (37 components, 2 μmol/L each) were confirmed in 6 repeated analyzes, they were 0.1% or less and 1.5% or less, respectively. A chromatogram of such D/L-amino acid standard solutions is shown in FIG. 4. In FIG. 4, the horizontal axis represents time and the vertical axis represents the signal strength of the detector.

Table 2 shows the evaluation results of the reproducibility of the retention time and area.

The numbers assigned to the peaks of the chromatogram in FIG. 4 correspond to the numbers assigned to the amino acid species in Tables 1 and 2.

In Tables 1 and 2, it means that the components written in italics are detected by OPA/NAC derivatization, and the components written in normal characters are detected by OPA/NIBC derivatization.

TABLE 2

| | アミノ酸種 | Retention time | Area | | アミノ酸種 | Retention time | Area |
|---|---|---|---|---|---|---|---|
| 1 | D-Asp | 0.23 | 1.50 | 19 | L-Asp | 0.35 | 1.32 |
| 2 | D-Glu | 0.09 | 0.47 | 20 | L-Glu | 0.09 | 0.44 |
| 3 | D-Asn | 0.09 | 0.29 | 21 | L-Asn | 0.09 | 0.26 |
| 4 | D-Ser | 0.10 | 0.19 | 22 | L-Ser | 0.10 | 0.19 |
| 5 | D-Gln | 0.09 | 0.26 | 23 | L-Gln | 0.10 | 0.29 |
| 6 | D-His | 0.07 | 0.40 | 24 | L-His | 0.06 | 0.40 |
| 7 | D-Thr | 0.06 | 0.25 | 25 | L-Thr | 0.07 | 0.35 |
| | | | | 26 | Gly | 0.07 | 0.41 |
| 8 | D-Arg | 0.02 | 0.19 | 27 | L-Arg | 0.02 | 0.18 |
| 9 | L-Ala | 0.03 | 0.49 | 28 | L-Ala | 0.03 | 0.54 |
| 10 | D-Tyr | 0.01 | 0.28 | 29 | L-Tyr | 0.02 | 0.28 |
| 11 | D-Val | 0.02 | 0.62 | 30 | L-Val | 0.01 | 0.37 |
| 12 | D-Met | 0.02 | 0.35 | 31 | L-Met | 0.01 | 0.35 |
| 13 | D-$(Cys)_2$ | 0.02 | 0.38 | 32 | L-$(Cys)_2$ | 0.02 | 0.62 |
| 14 | D-Trp | 0.05 | 0.42 | 33 | L-Trp | 0.05 | 0.44 |
| 15 | D-Ile | 0.02 | 0.38 | 34 | L-Ile | 0.06 | 0.72 |
| 16 | D-Phe | 0.06 | 0.51 | 35 | L-Phe | 0.06 | 0.52 |
| 17 | D-Leu | 0.02 | 0.30 | 36 | L-Leu | 0.02 | 0.31 |
| 18 | D-Lys | 0.02 | 0.50 | 37 | L-Lys | 0.02 | 0.43 |

*斜体*: OPA/NAC*誘導体化*
常体: OPA/NIBC誘導体化

That is, D-Asp, D-Arg, D-Ala, D-Trp, D-Phe, L-Asp, L-Arg, L-Ala, L-Trp, L-Ile, L-Phe derivatized by OPA/NAC were detected, and on the other hand, D-Glu, D-Asn, D-Ser, D-Gln, D-His, D-Thr, D-Tyr, D-Val, D-Met, D-(Cys) 2, D-Ile, D-Leu, D-Lys, L-Glu, L-Asn, L-Ser, L-Gln, L-His, L-Thr, Gly, L-Tyr, L-Val, L-Met, L-(Cys) 2, L-Leu, L-Lys derivatized by OPA/NIBC were detected.

As described above, in a highly preferable embodiment of the present method, two kinds of derivatization reagents, OPA/NAC and OPA/NIBC, were used, and the conditions of the mobile phase for each derivatization reagent were set by using the phosphoric acid-based buffer as the mobile phase A as described above and the mixed solvent systems of water, acetonitrile and methanol as mobile phase B in which only the solvent mixing ratio is different for each derivatization reagent, and the HPLC analytical conditions other than the gradient conditions of the mobile phase A and the mobile phase B could be made the same (common).

Therefore, when the analysis of the derivatized sample 1 by OPA/NAC is completed and the analysis of the derivatized sample 2 is performed, by automatically changing the mixing ratio of water, acetonitrile and methanol in the mobile phase blending unit to prepare mobile phase B and switching the analytical method that automatically controls the gradient condition 1 in the analysis of the derivatized sample 1 and the gradient condition 2 in the analysis of the derivatized sample 2, the analytical conditions can be easily changed without any hassle. The total of 37 components of D/L-amino acids constituting the protein in the sample are well separated and can be identified and quantified accurately.

In addition, the analysis of the amino acids of 37 components can be performed in a total analysis time of 130 minutes.

INDUSTRIAL APPLICABILITY

The analytical method of the present invention can easily analyze D/L-amino acids in a sample with high reproducibility, and in particular, can analyze L-amino acids and D-amino acids constituting a protein all at once. Therefore, it is useful for amino acid analysis in various food analysis fields including brewed sake such as beer, rice wine, and wine.

DESCRIPTION OF REFERENCES

100 . . . Liquid chromatograph analysis system
10 . . . Mobile phase blending unit
11, 11*a*, 11*b*, 11*c*, 11*d* . . . Mobile phase container
12 . . . Mixer
20 . . . Liquid feeding unit
21A, 21B . . . Liquid feeding pump
22 . . . Mixer
30 . . . Autosampler
31*a*, 31*b* . . . Derivatization reagent
32 . . . Analysis sample
33 . . . Autoinjector
40 . . . Column oven
41 . . . Column
50 . . . Detector
60 . . . Control unit
70 . . . Display

What is claimed is:

1. A method for analyzing amino acids by liquid chromatography, in which a sample containing a plurality of kinds of amino acids is derivatized with a derivatization reagent, and the obtained derivatized sample is passed on a column together with a mobile phase system, wherein the mobile phase system is composed of a plurality of mobile phases, and at least one mobile phase of the plurality of the mobile phases is a mixed solvent system, wherein two or more kinds of derivatized samples are prepared using two or more kinds of derivatization reagents, wherein different analytical conditions in which mixing ratio of the plurality of the mobile phases is changed with a passage of time are set for each kind of the derivatization reagent, and a solvent mixing ratio of solvents in the mixed solvent system is varied for the each kind of the derivatization reagent, and wherein the two or more kinds of derivatized samples are analyzed by automatically switching between the different analytical conditions and the solvent mixing ratios to separate and quantify derivatized L-amino acids and derivatized D-amino acids.

2. The method as claimed in claim 1, wherein aspartic acid, glutamic acid, asparagine, serine, glutamine, histidine, threonine, arginine, alanine, tyrosine, valine, methionine, cystine, tryptophan, isoleucine, phenylalanine, leucine, lysine, and glycine are analyzed as the amino acids.

3. The method as claimed in claim 1, wherein the plurality of the mobile phases are composed of two kinds, mobile phase A and mobile phase B, and wherein for the each kind of the derivatization reagent, analytical conditions that change the mixing ratio of the mobile phase A and the mobile phase B with the passage of time are set, and the different analytical conditions are automatically switched to analyze the two or more kinds of derivatized samples.

4. The method as claimed in claim 3, wherein the mobile phase A is a buffer solution, and the mobile phase B is a mixed solvent system.

5. The method as claimed in claim 3, wherein the mobile phase B is the mixed solvent system of water, acetonitrile and methanol, and the solvent mixing ratio is varied for the each kind of the derivatization reagent and is automatically switched for each analysis of the two or more kinds of derivatized samples.

6. The method as claimed in claim 1, wherein two kinds of a mixture of o-phthalaldehyde and N-acetyl-L-cysteine and a mixture of o-phthalaldehyde and N-isobutyryl-L-cysteine are used as the derivatization reagent.

7. The method as claimed in claim 1, wherein derivatization of the sample is performed by an automatic sample introduction device having a pretreatment function.

8. The method as claimed in claim 1, wherein a pH of the mobile phase passing in the column is 7-12.

9. The method as claimed in claim 1, wherein the mobile phase system comprises mobile phase A and mobile phase B, wherein mobile phase A is a buffer solution and mobile phase B is a mixed solvent system comprising at least solvent B1 and solvent B2, wherein the solvent mixing ratio of the at least solvent B1 and solvent B2 in mobile phase B is varied depending on each kind of the derivatization reagent, and wherein different analytical conditions, in which the mixing ratio of mobile phase A and mobile phase B is varied over time, are set for each kind of the derivatization reagent.

10. The method as claimed in claim 9, wherein the mobile phase B is a mixed solvent system comprising solvent B1, solvent B2, and solvent B3, and wherein the solvent mixing ratio of the solvent B1, solvent B2, and solvent B3 in mobile phase B is varied depending on each kind of the derivatization reagent.

* * * * *